| United States Patent [19] | [11] | 4,008,251 |
|---|---|---|
| Moore et al. | [45] | Feb. 15, 1977 |

[54] REACTION OF ALKYLADAMANTANE COMPOUNDS TO FORM PRODUCTS HAVING TWO LINKED ADAMANTANE NUCLEI

[75] Inventors: Robert E. Moore, Wilmington, Del.; Abraham Schneider, Overbrook Hills, Pa.

[73] Assignee: Sun Oil Company, (Sun Research and Development Co.), Marcus Hook, Pa.

[22] Filed: July 20, 1970

[21] Appl. No.: 56,680

Related U.S. Application Data

[63] Continuation-in-part of Ser. No. 851,488, Aug. 19, 1969, abandoned.

[52] U.S. Cl. .............................. 260/333; 260/335; 260/666 M; 252/52 R; 252/59; 252/73
[51] Int. Cl.$^2$ ............ C07D 313/14; C07D 311/80; C07C 13/54;
[58] Field of Search ............... 260/333, 335, 666 M

[56] References Cited
OTHER PUBLICATIONS

M. A. McKervey et al., Tetrahedron Letters No. 50, (1968) pp. 5165–5168.
H. W. Geluk et al., Tetrahedron, vol. 24 (1968) pp. 5361–5368.
H. W. Geluk et al., Rec. Trav. Chim., vol. 88 (1969) pp. 13–16.

*Primary Examiner*—Norma S. Milestone
*Attorney, Agent, or Firm*—J. Edward Hess; Donald R Johnson; Stanford M. Back

[57] ABSTRACT

Alkyladamantanes and/or alkyladamantanols of the $C_{12}$–$C_{19}$ range containing 1–3 alkyl groups of the $C_1$–$C_3$ range are converted to hydrocarbon dimers in which two adamantane nuclei are linked to each other through an alkylene radical derived from and having the same number of carbon atoms as an alkyl group of the starting material. The reaction is effected by contacting the starting material with sulfuric acid having a strength in the range of 94–102% $H_2SO_4$ in the absence of any other reactant material. When the reactant is a dimethyladamantane or ethyldimethyladamantane or a monool corresponding thereto, ether products in which two adamantane nuclei are joined both through an ether linkage and through a methylene or ethylene radical can also be produced. Some of the linked products are oily liquids while others are normally solid. Usually a small amount of alkyladamantanone is formed. Both the hydrocarbon dimers and ethers have unusually high traction coefficients and are particularly useful as component of traction fluids. These products also have various other uses, such as in coating, investment casting, caulking and potting compositions and as stiffening agents in candles.

24 Claims, No Drawings

REACTION OF ALKYLADAMANTANE COMPOUNDS TO FORM PRODUCTS HAVING TWO LINKED ADAMANTANE NUCLEI

CROSS REFERENCES TO RELATED APPLICATIONS

This application is a continuation-in-part of our co-pending application, Ser. No. 851,488, filed Aug. 19, 1969 and now abandoned.

Application Ser. No. 784,487, filed Dec. 17, 1968, by Robert E. Moore, now U.S. Pat. No. 3,646,224, issued Feb. 29, 1972, discloses and claims the preparation of bridgehead monools in high yields from alkyladamantanes by dissolving an alkyladamantane at a temperature below 50° C. in fuming sulfuric acid having a strength above 102% $H_2SO_4$ equivalent and then reacting the mixture with water to form a bridgehead monool corresponding to the starting alkyladamantane.

Application Ser. No. 823,138, filed May 8, 1969, by Abraham Schneider, now U.S. Pat. No. 3,560,578, issued Feb. 2, 1971, discloses a reaction for linking adamantane nuclei between bridgehead positions through a trimethylene or tetramethylene radical. The procedure involves reacting the adamantane hydrocarbon with a propyl or butyl chloride or bromide using $AlCl_3$ or $AlBr_3$ as catalyst. Some of the products that can be made by this procedure are analogous to, and can be used for similar purposes as, some of the products obtainable by the process of the present invention.

Application Ser. No. 877,004, filed Nov. 14, 1969, by Robert E. Moore, now abandoned, relates to the reaction of adamantane hydrocarbons or adamantanols with n-paraffins in the presence of sulfuric acid having a strength of 92–102% $H_2SO_4$ equivalent, whereby the adamantane nucleus is alkylated by means of the n-paraffin reactant to give hydrocarbon products containing an alkyl or alkylene group derived from and having the same number of carbon atoms as the n-paraffin.

BACKGROUND OF THE INVENTION

This invention relates to the conversion of $C_{12}$–$C_{19}$ alkyladamantane hydrocarbons in which the alkyl groups are of the $C_1$–$C_3$ range and/or their corresponding monools to compounds having two linked adamantane nuclei per molecule. For convenience, these linked compounds are herein referred to as "bistype" products. They include hydrocarbon products in which the adamantane nuclei are coupled to each other solely through an alkylene linkage and also certain oxygen-containing products wherein the nuclei are joined not only through a methylene or ethylene linkage but also through an ether linkage.

The adamantane nucleus has ten carbon atoms, four of which are bridgehead carbons that are equivalent to each other, as can be seen from the following typographical representation:

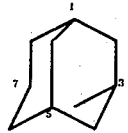

As shown, the bridgehead carbon atoms customarily are designated by the numerals 1, 3, 5 and 7 respectively, and these bridgehead positions are all equivalent to each other in the nuclear structure.

Starting materials for the present process are alkyladamantanes and/or alkyladamantanols of the $C_{12}$–$C_{19}$ range. The starting reactant can have one, two or three alkyl substituents on the adamantane nucleus, such substituents being of the $C_1$–$C_3$ range. In other words, the alkyl substituents can be methyl, ethyl, n-propyl or isopropyl. Methods of preparing these feed materials are known in the prior art.

The preparation of methyl- and/or ethyl-substituted adamantanes by the isomerization of tricyclic naphthenes by means of an aluminum halide or $HF$-$BF_3$ catalyst has been described by several references including the following: Schneider U.S. Pat. No. 3,128,316, dated Apr. 7, 1964; Janoski and Moore U.S. Pat. No. 3,275,700, dated Sept. 27, 1966; Schneider et al. U.S. Pat. Nos. 3,336,405 and 3,336,406, dated Aug. 15, 1967; Schneider U.S. Pat. No. 3,356,751, dated Dec. 5, 1967; Schleyer et al., Tetrahedron Letters No. 9, pps. 305–309 (1961); and Schneider et al., JACS, 86, pps. 5365–5367 (1964). The isomerization products can have the methyl and/or ethyl groups attached to the adamantane nucleus at either bridgehead or nonbridgehead positions or both, although completion of the isomerization reaction favors bridgehead substitution. Examples of alkyladamantanes made by such isomerization are dimethyladamantanes, ethyladamantanes, methylethyladamantanes, dimethylethyladamantanes and trimethyladamantanes.

Preparations of adamantane hydrocarbons having $C_3$ or higher alkyl substituents have been described in the following references: Schneider U.S. Pat. No. 3,382,288, dated May 7, 1968; and Spengler, et al., Erdol und Kohle-Erdgas-Petrochemie, Vol. 15, pp. 702–707 (1962).

Procedures for converting adamantane hydrocarbons to bridgehead hydroxy derivatives have been described in the prior art. Schneider U.S. Pat. No. 3,356,740, dated Dec. 5, 1967, discloses the conversion of alkyladamantanes to bridgehead alcohols by air oxidation using a soluble metallic organic salt as catalyst, as also does Schneider U.S. Pat. No. 3,450,775, dated June 17, 1969. Moore U.S. Pat. No. 3,383,424, dated May 14, 1968, shows the oxidation of alkyladamantanes by means of chromic acid in aqueous acetic acid under conditions to produce either monools or diols.

The preparation of nonbridgehead adamantanols containing nonbridgehead alkyl groups from adamantanone and their conversion to the corresponding non-bridgehead alkyladamantanes have been described by Landa et al., Collection Czechoslov. Chem. Commun.,-/Vol. 32/(1967).

Alkyladamantanols in which the hydroxy group is at a nonbridgehead position can be made similarly from keto derivatives of alkyladamatanes which are obtained as by-products of the air oxidation process disclosed in aforesaid Schneider U.S. Pat. No. 3,356,740. Conversion of the keto group can be carried out by a Grignard synthesis in the manner described in the aforesaid Landa et al. reference or by Schleyer et al., JACS, 83, 186, which shows the reaction of adamantanone with methyl iodide and magnesium to yield 2-methyladamantanol-2. In analogous fashion the keto by-products of U.S. Pat. No. 3,356,740 can be converted to nonbridgehead alkyladamantanols also having at the nonbridgehead position an ethyl, n-propyl or isopropyl substituent in addition to the alkyl substituents that were present in the starting alkyladamantane hydrocarbon.

In the prior art, the preparation of two bis-type adamantane hydrocarbons having an ethylene linkage between the nuclei has been described by Stepanov and Baklan, J. GEN. CHEM. USSR, Vol. 34(2), pages 580–584 (1964). Specifically, these compounds were 1,2-bis(adamantyl-1)-ethane and 1,2-bis(1-methyladamantyl-3)-ethane, both being high melting solids having melting points, respectively, of 289° C. and 153° C. They were made from 1-hydroxymethyladamantane by classical synthesis techniques involving Grignard reactions, the reaction routes being entirely different from reactions which occur in the process of the present invention.

Reinhardt U.S. Pat. No. 3,342,880, dated Sept. 19, 1967, discloses the coupling of adamantylamide molecules together through a methylene linkage by a reaction also quite different from reactions of the present process. Specifically, this coupling was effected by reaction of the adamantylamide with formaldehyde in the presence of strong sulfuric acid, and the resulting methylene linkage was attached to each of the coupled adamantane nuclei at a bridgehead position.

SUMMARY OF THE INVENTION

Alkyladamantanes and/or alkyladamantanols of the $C_{12}$–$C_{19}$ range having 1–3 alkyl substituents of the $C_1$–$C_3$ range (i.e., methyl, ethyl, n-propyl or isopropyl) are reacted to form bistype products by contacting the feed reactant with strong sulfuric acid having a strength in the range of 94–102% $H_2SO_4$ equivalent by weight, more preferably 96–100% $H_2SO_4$. The temperature of contacting is between the freezing point of the sulfuric acid and 100° C., more preferably in the range of 10°–75° C. These conditions cause the alkyladamantane feed compounds to react in a manner to form dimer hydrocarbon products having two adamantane nuclei linked through an alkylene radical corresponding to an alkyl group of the feed compound. In other words, the linkage moiety between the nuclei can be represented by —R—, wherein R is an alkylene radical having the same number of carbon atoms as an alkyl substituent of the starting compound. If the latter contains only methyl substituents, the resulting linkage is attached to a nonbridgehead carbon of one of the nuclei and a bridgehead carbon of the other; whereas if an ethyl or propyl substituent is present, the resulting ethylene or trimethylene linkage is attached only to bridgehead positions of the linked nuclei.

When the feed material contains a dimethyladamantane, dimethyladamantanol, ethyldimethyladamantane or ethyldimethyladamantanol, another type of product is also obtained which contains an ether linkage. These ether compounds also are referred to herein, for convenience, as "bis-type" products since they contain two adamantane nuclei per molecule. The nuclei are joined both through an —R— linkage, wherein R is methylene or ethylene, and through the ether linkage as more fully described hereinafter. As a result, the ether compounds contain one more ring per molecule than the dimer hydrocarbon bis-type compounds.

Many of the bis-type products of the present process, including both the dimer hydrocarbons and the ethers, are oils at room temperature and exhibit unusually high traction coefficients. They are particularly useful as components of traction fluids for use in friction drive or toric transmission systems. Some of the bis-type products have sufficient symmetry to be relatively high melting solids, and these have utility as components in compositions for coating, investment casting, caulking and potting and for various other purposes.

DESCRIPTION

The reactant material for the present process can be one or more alkyladamantane hydrocarbons of the $C_{12}$–$C_{19}$ range having one, two or three alkyl substituents of the $C_1$–$C_3$ range or, in other words, having 1–3 substituents which can be methyl, ethyl, n-propyl, isopropyl or combinations of these alkyl radicals. These substituents can be in bridgehead or nonbridgehead positions or both on the adamantane nucleus. Starting materials which contain no higher substituent than methyl contain 2–3 substituents, or in other words are dimethyladamantanes or trimethyladamantanes. As an alternative feed, any alkyladamantanol corresponding to the feed hydrocarbons as specified above and having the hydroxy group positioned on the nucleus at either a bridgehead or nonbridgehead position can be used. Also mixtures of such alkyladamantanols and alkyladamantane hydrocarbons can be employed as the feed material.

The following are specific examples of alkyladamantane hydrocarbons that can be used in the process: 1,3- or 1,4- or 2,6-dimethyladamantane; 1- or 2-ethyladamantane; 1-ethyl-3-methyl- or 1-ethyl-4-methyladamantane; 1-methyl-4-ethyladamantane; 1- or 2-n-propyladamantane; 1- or 2-isopropyladamantane; 1-methyl-4-propyladamantane; 1,3,5- or 1,3,6-trimethyladamantane; 1,3- or 1,4-diethyladamantane; 1,3- or 1,4-dipropyladamantane; 1-ethyl-3,5-dimethyl- or 1,3-dimethyl-6-ethyladamantane; 1,3,5-triethyladamantane; 1,3-diethyl-5-isopropyladamantane; 1,3,5-tripropyladamantane; and the like. Likewise, any alkyladamantanol corresponding to the foregoing hydrocarbons and having its hydroxy group located at a bridgehead or nonbridgehead position on the nucleus can be employed as the feed reactant.

Reaction of the alkyladamantane and/or alkyladamantanol feed material in accordance with the invention is effected by contacting same with strong sulfuric acid in the absence of any other reactant material. The sulfuric acid should have a strength in the range of 94–102% $H_2SO_4$ equivalent by weight and more preferably 96–100% $H_2SO_4$. The reaction temperature can be from just above the freezing point of the acid used to about 100° C. and usually is in the range of 10°–75° C. Contact of the acid with the feed material causes the latter to react in an unexpected manner, whereby dimer hydrocarbon products are formed in which two adamantane nuclei are linked to each other through an alkylene radical (—R—) derived from and having the same number of carbon atoms as an alkyl group of the starting reactant.

In the case of certain feed compounds, viz. dimethyladamantanes, ethyldimethyladamantanes and their corresponding adamantanols, the reaction can also surprisingly yield bis-type products which are ethers, wherein the adamantane nuclei are joined through two linkages as follows: (1) an alkylene radical (—R—) which is methylene or ethylene and (2) an ether linkage (—O—). These products have one more ring per molecule than the bis-type hydrocarbon products, with such ring having either six or seven member atoms, including one oxygen atom, depending upon the feed compound used. This formation of products with ether linkages curiously does not seem to occur with any of the other alkyladamantane feed compounds of the class above specified.

When the starting material contains only methyl substituents, the linkage moiety in the dimer hydrocarbon product is a methylene radical. One of its valences is attached to a bridgehead carbon atom in one nucleus, while its other valence is attached to a nonbridgehead carbon atom in the other nucleus. Linkage of the nuclei in this fashion occurs even when all methyl substituents in the feed material are located at bridgehead positions. By way of illustration, Equation 1 shows what results when 1,3-dimethyladamantane is reacted to form the dimer hydrocarbon product. (For convenience herein, hydrogen atoms are omitted and equations are left unbalanced).

When dimethyladamantanes are used that have one or two nonbridgehead methyl substituents in place of 1,3-dimethyladamantane, the same two dimer isomers are produced. This comes about evidently because the methyl substituents migrate to the 1,4-positions, following which the abstraction of hydrogen from the 4-position carbon atoms occurs followed by linkage through this carbon atom to a bridgehead position of the other nucleus. When the starting material is 1,4-dimethyladamantane or its corresponding monools, methyl group migration does not need to occur in order to form these isomeric dimer products.

If the starting material contains an ethyl group and no higher alkyl substituent, linkage between the adamantane nuclei occurs mainly through an ethylene radical regardless of whether one or more methyl substituents are present or not. Especially does practically all link- Eq. 1:

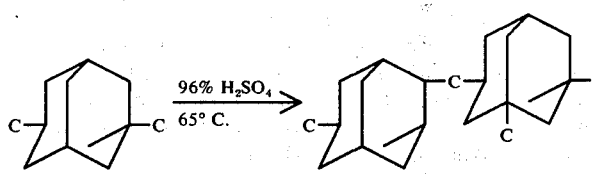

From the equation it can be seen that the left-hand nucleus of the reaction product is attached to the methylene radical at a nonbridgehead (or secondary) carbon atom whereas the other nucleus is linked at a bridgehead (or tertiary) position. Since both methyl group carbon atoms originally were located at bridgehead positions in the feed, this means that the reaction mechanism involved a migration of one of the methyl groups to a nonbridgehead position. The product in this case is actually a mixture of two geometric isomers (anti and syn) occurring in roughly equal amounts, which are close boiling but which can be separated from each other by GLC in a suitably efficient chromatographic column. Specifically, these two isomers are the following compounds:

syn-4-(3,5-dimethyl-1-adamantyl)methyl-1-methyladamantane anti-4-(3,5-dimethyl-1-adamantyl)methyl-1-methyladamantane These compounds are excellent components for traction fluid compositions.

age take place through the ethylene radical if the methyl groups are located only at bridgehead positions, inasmuch as any linkage via methylene would first require isomerization of a methyl group to a nonbridgehead position which isomerization is a slow reaction compared to reaction of the ethyl group. Another reaction that occurs when the starting material contains an ethyl group is that the latter to some extent transalkylates between adamantane nuclei. Consequently the bis-type products obtained generally include dimers having 0, 1 and 2 ethyl substituents.

With an ethyl group located at a nonbridgehead carbon atom in the starting material, linkage between adamantane nuclei can occur from the nonbridgehead carbon of one nucleus to a bridgehead position in the other through the ethylene radical formed from the ethyl group. Also some isomerization of the ethyl group to a bridgehead position may take place before linkage occurs, thus resulting also in linkage between bridgehead positions in the respective nuclei.

Results obtained when the starting material contains an ethyl substituent are illustrated by Equation 2 for the reaction of 1-ethyl-3-methyladamantane.

Eq. 2:

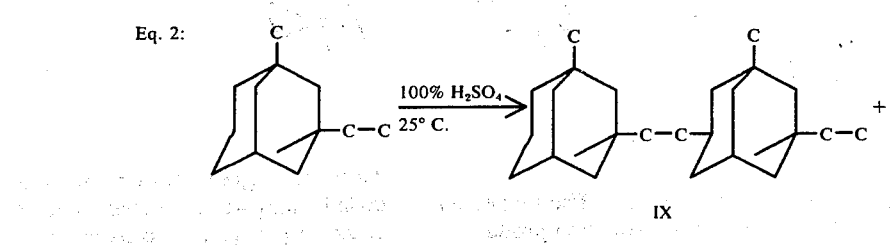

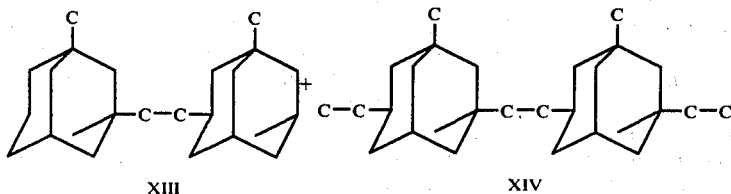

XIII          XIV

Of the bis-type products in Equation 2, the one first-shown having one ethyl substituent is the direct product of the dimerization reaction, while the second and third having none and two ethyl substituents, respectively, are the results of transalkylation. These three bis-type products specifically are the following compounds, listed in the order shown in Equation 2:

1-(3-methyladamantyl-1)-2-(3'-methyl-5'-ethyladamantyl-1')ethane 1,2-bis(3-methyladamantyl-1)ethane 1,2-bis(3-methyl-5-ethyladamantyl-1)ethane The compound with one ethyl substituent is the predominant reaction product and constitutes the main component of the dimer product obtained. This compound in pure form is an oily liquid at room temperature, while the other two, more symmetrical product compounds are normally solids when pure. However, when these compounds are recovered from the reaction product in admixture with each other, the mixture is normally an oily liquid that can be used as a component in traction fluid compositions.

When the starting material contains a propyl group with or without methyl substituents, the linkage moiety between the nuclei mainly corresponds to the propyl group. Thus an n-propyl group gives a trimethylene linkage and an isopropyl group tends to result in a methylethylene linkage. Also disproportionation of propyl substituents between the nuclei can occur to some extent, yielding products analogous to those shown in Equation 2. Thus the reaction of 1-n-propyl-3,5-dimethyladamantane gives the bis-type products shown in Equation 3.

an oily liquid at room temperature when pure. The second- and third-listed compounds, which result from transalkylation, are normally solids when isolated, having melting points of 71°–75° C. and 80°–84° C., respectively. However, the mixture of bis-type compounds recovered from the reaction mixture is an oily liquid useful as a traction fluid component. In this reaction there is also obtained a small amount of 1,3-di-n-propyl-5,7-dimethyladamatane, resulting from transalkylation without dimerization. This compound in pure form also is normally a liquid and, if desired, can be included in the mixed product for use as traction fluid material.

When both ethyl and propyl substituents are present in the starting material, products are obtained having linkage moieties derived from each. For example, 1-propyl-3-ethyladamantane gives hydrocarbon dimers having a trimethylene linkage and other dimers having an ethylene linkage between the nuclei. Due to disproportionation of both ethyl and propyl groups, dimer products containing two ethyl groups, or two propyl groups, or both an ethyl and a propyl group are also produced in minor amounts.

As pointed out above, bis-type products which are ethers can be obtained in addition to the hydrocarbon dimers when the reactant material is a dimethyladamantane, an ethyldimethyladamantane or their corresponding bridgehead monools. The ethers producible from these starting materials in accordance with the invention are of the $C_{24}$–$C_{30}$ range. Formation of the ether products generally is favored by the use of relatively high acid strength within the range specified, e.g., 98–101% $H_2SO_4$. By way of example, Equation 4 shows Eq. 3:

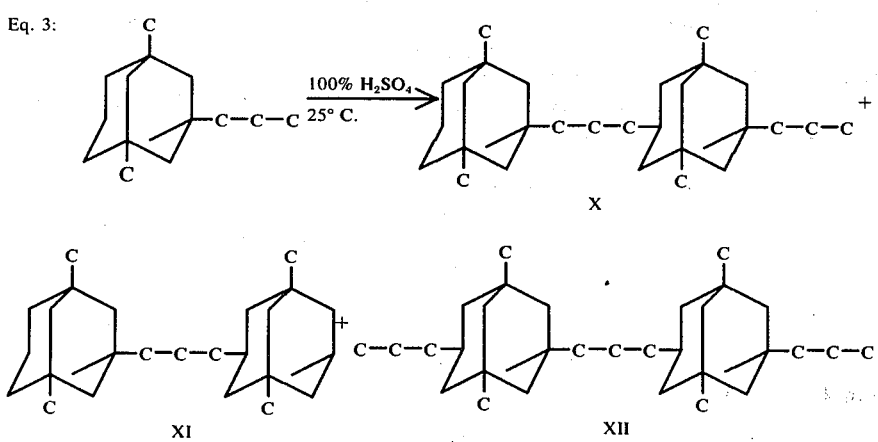

X

XI          XII

No ethers are formed in this reaction. The first-listed compound, which is the direct dimerization product, is the bis-type products that are formed when 1,3-dimethyladamantane is reacted under conditions for producing ethers as well as hydrocarbon dimers.

Eq. 4:

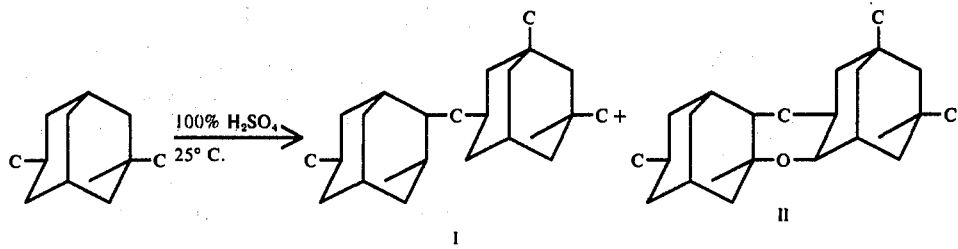

As shown, the ether product obtained is analogous to the hydrocarbon dimer product except that additionally there is an ether linkage between bridgehead and nonbridgehead carbon atoms of the two adamantane nuclei. This results in an additional six-membered ring in the molecule, as compared to the hydrocarbon dimer. Each has 24 carbon atoms in this case. The ether product occurs in the form of a plurality of stereoisomers that fall into two types, namely, cis-type isomers and trans-type isomers differing in the spatial relationships of the rings to each other. This can be illustrated by the following structural formulas for the ring systems (omitting the three methyl substituents):

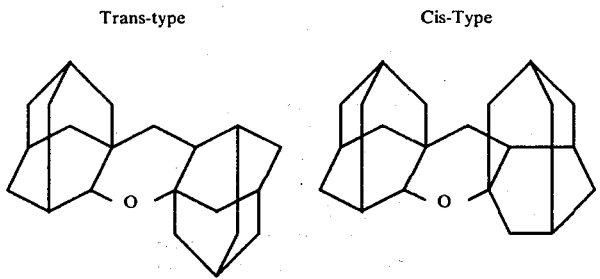

Trans-type          Cis-Type

In each type a plurality of isomers occur which differ by the positions of the three methyl substituents on the adamantane nuclei. The methyl groups are all attached to bridgehead carbon atoms, with two methyl groups on one nucleus and the third on the other, but the possible variations of their positions relative to the oxygen atom permits a plurality of isomers of both the trans-type and the cis-type.

These various ether isomers boil on the order of 25° C. higher than the dimer isomers, and, like the dimer isomers, boil closely to each other. The cis-type and trans-type isomers generally will appear as separate peaks from a gas-liquid chromatographic column and can be separately collected if desired. However the individual isomers of each type boil so closely together that recovery of the individual compounds would be impracticable. These ether products also have high traction coefficients and are excellent components of traction fluids.

The structure of the ethers from dimethyladamantane (DMA), as shown in Formula II of Equation 4, is consistent with test data obtained on this product by NMR, IR and mass spectroscopy as well as data obtained upon derivatizing the product by cleaving the ether linkage with acetic anhydride in the presence of $BF_3$-etherate to form acetate and hydroxy groups. Mass spectroscopy shows the molecular weight to be 340 as required for Formula II, and NMR reveals the methylene group and also indicates only one proton on the carbon atoms to which the oxygen atom is linked, thus showing that the ether linkage extends between bridgehead and nonbridgehead carbon atoms. The acetate-containing derivative from derivatization in the manner indicated has a higher molecular weight than the ether product, which would not be the case if the adamantane nuclei were joined by only an ether linkage.

The ethers produced when ethyldimethyladamantane (EDMA) is the reactant material likewise have two adamantane nuclei joined through two linkages, viz. an ether linkage and an alkylene linkage, to form an additional ring. There are several differences, however, between these ethers and those obtained from dimethyladamantane (DMA) as described above. For EDMA the resulting alkylene linkage is ethylene instead of methylene, and it joins each nucleus at a bridgehead position instead of extending between bridgehead and nonbridgehead carbon atoms as in the case of the methylene linkage. Also the ether linkage is between two nonbridgehead positions of the respective nuclei, whereas the ether linkage obtained from DMA extends from a bridgehead of one nucleus to a nonbridgehead carbon atom of the other. The resulting new ring in the case of EDMA thus contains seven instead of six member atoms.

The EDMA ethers also differ from those obtainable from DMA in that the cis-type and trans-type configurations, as discussed above for the DMA ethers, do not apply. Only one ring structure arrangement is exhibited by the ethers obtained from EDMA, so that they do not tend to appear as two distinct peaks in GLC analysis. Again, however, these ethers include a plurality of isomers resulting from various arrangement of the alkyl substituents at available bridgehead positions on the nuclei relative to the oxygen atom in the ether linkage. Furthermore, due to the occurrence of transalkylation the ether products, just as in the case of the dimer hydrocarbons, include ether compounds having none, one and two ethyl substituents and 26, 28 and 30 carbon atoms, respectively. For example, the ether products obtained from 1-ethyl-3,5-dimethyladamantane include compounds having each of structures VI, VII and VIII as shown below:

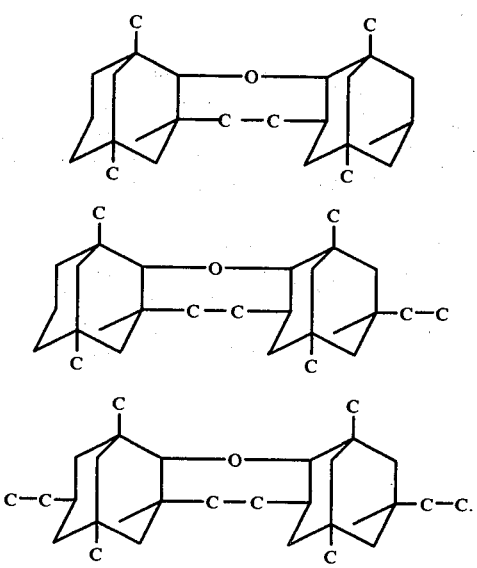

Each of these ethers boils on the order of 5°–10° C. higher than the corresponding hydrocarbon dimer.

Results analogous to those obtainable with the alkyladamantane hydrocarbons can be secured by substituting corresponding alkyladamantanols as the starting material. Generally these monools are more reactive than the alkyladamantanes so that similar results can be obtained by using lower acid concentrations and/or lower reaction temperatures within the ranges specified. The starting monool can have the hydroxy group either at a bridgehead or nonbridgehead position. These are equivalent inasmuch as the nonbridgehead hydroxy substituent immediately isomerizes to a bridgehead position in the presence of the strong acid medium. Mixtures of one or more alkyladamantanes with one or more alkyladamantanols can be used if desired.

The monools of 1,3-dimethyladamantane under certain conditions (e.g., 100% $H_2SO_4$; 25° C.) can yield a minor but substantial amount of an olefinic dimer in addition to the kinds of products already described. Conditions for maximizing this product comprise high acid strength (e.g., 99–102% $H_2SO_4$), low temperature (e.g., 10°–25° C.) and relatively short reaction times. In this olefinic dimer the two adamantane nuclei are linked through a methine radical in the following fashion:

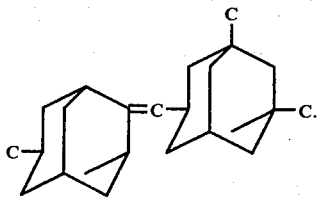

Specifically this compound is 4-(3,5-dimethyl-1-adamantyl)methylene-1-methyladamantane. If desired, it can be hydrogenated to yield a mixture of the two saturated geometric isomers obtained from dimethyladamantane as described above.

Besides the hydrocarbon dimers and ethers other compounds which may be present in the reaction product are alkyladamantanones, alkyladamantanols, and monomeric adamantane hydrocarbons having more and less carbon atoms than the feed due to the transfer of ethyl or propyl groups by transalkylation. These products usually are present only in small amounts, except in some cases when the feed is dimethyladamantane and/or dimethyladamantanol. The former can yield a reaction product, if the reaction mixture is quenched with water before sufficient reaction has been allowed, that contains a substantial amount of dimethyladamantanol in addition to the dimers and ethers. When the feed comprises dimethyladamantanol, there is a tendency to produce substantial amounts of corresponding alkyladamantanones, especially if a relatively low acid strength is employed, say about 94–97% $H_2SO_4$, with temperatures in the range of 20°–70° C. These generally include two or more isomers, with the isomer tending to predominate in which the keto group is located most remotely from the methyl substituents. For example, from 3,5-dimethyladamantanol-1 the following isomers can be formed, the first-listed one predominating:

5,7-dimethyladamantanone-2
1,5-dimethyladamantanone-2
1,3-dimethyladamantanone-2.

If desired, a mixture of these adamantanones can be recovered as a separate fraction from the reaction product. From such mixture the first-listed ketone can be separated by GLC or fractional crystallization, this isomer being a solid with a melting point of 66°–67° C. The other two isomers are so close boiling as to be difficult to separate from each other but are readily obtainable as a mixture which is liquid at room temperature. These ketones can be converted to nonbridgehead amines by known techniques as shown, for example, in Smith U.S. Pat. No. 3,257,456, issued June 21, 1966, which describes the conversion of adamantanone-2 to nonbridgehead amines that exhibit antiviral activities. Alkyladamantyl amines made in analogous fashion from the isomers listed above exhibit similar antiviral activities.

The present process is carried out by admixing the alkyladamantane and/or alkyladamantanol reactant material with the strong sulfuric acid at a selected temperature within the range herein specified and in the absence of any other reactant material. The ratio of acid to reactant can vary widely. Generally a volume excess of the acid relative to the reactant should be used and a volume ratio thereof in the range of 1:1 to 20:1 typically is employed. When the reactant is an alkyladamantane hydrocarbon, the reaction mixture will be composed of an acid phase and a hydrocarbon phase, and the system should be well agitated to provide good contact between the phases. On the other hand, when the starting reactant is an alkyladamantanol, it readily dissolves in the acid phase and the mixture does not necessarily need to be stirred as vigorously. In any event contacting of the materials is continued at least until substantial linkage of adamantane nuclei has occurred. Suitable reaction times are illustrated by specific examples shown hereinafter. The linked material is thereafter recovered as product of the process.

The dimer hydrocarbon product is essentially insoluble in the acid phase and can be separated therefrom by settling or centrifuging. Any unreacted hydrocarbon feed as well as hydrocarbon transalkylation products will separate along with the dimers. If desired, the reaction mixture can be extracted with an inert solvent such as n-pentane to facilitate separation of these hydrocarbon materials from the acid phase. The pentane can then be evaporated from the extract and the residue fractionally distilled to separate the individual components.

The ether products formed during the reaction practically all remain in the acid phase when the acid strength is 98% $H_2SO_4$ or greater. This is fortunate since it simplifies the recovery of the ethers and hydrocarbon dimers separately when these are desired as separate products. On the other hand, at an acid strength of 96% or lower most of the ethers tend to go into the hydrocarbon phase, while at 97% the ethers tend to partition between the two phases. Consequently, when the reaction has been carried out using an acid strength below 98% $H_2SO_4$, it is advantageous in the recovery stage to add enough strong (e.g., fuming) sulfuric acid to bring the average strength up to above 98%, contact the hydrocarbon and acid layers to cause substantially all of the ethers to dissolve in the fortified acid phase, and then separate the phases. The ethers and dimers can then be readily recovered as separate products. In cases where it is desired to recover these in admixture with each other, as when both are to be used as traction fluid material, it is best to regulate the acid strength to 96% or lower by adding water, if necessary, so that essentially all of the ethers will go into the hydrocarbon phase before the phases are separated. Any ketones formed during the reaction tend to stay in the acid layer. The hydrocarbon phase can then be distilled to remove all components boiling below the lowest boiling hydrocarbon dimer, thus leaving a mixture of dimers and ether as residue. This mixture will have a high traction coefficient and can be used, without further separation, in traction fluid compositions. Alternatively, the residue can be vacuum distilled to obtain cuts each composed of a hydrocarbon dimer and its corresponding ether, which cuts can be used separately if desired in the formulation of traction fluid compositions. Any combination of the individual dimer and/or ether compounds can likewise be used for this purpose.

Recovery of the ethers from the acid phase when present therein can be achieved by diluting the acid with water (or ice) to about 20-30% $H_2SO_4$ and settling the mixture. This causes the ethers to separate as an oily phase. Any ketones that had been formed will also be present in this oily phase. If desired, the diluted acid phase can be extracted with a suitable solvent (e.g., diethyl ether) to insure removal of the ether and ketone products, followed by evaporation of the solvent. The ketones can readily be separated from the ether products by vacuum distillation, since the latter are considerably higher boiling than the ketones. If desired, ethers having different numbers of carbon atoms, e.g., $C_{26}$, $C_{28}$ and $C_{30}$, as obtained when the feed is ethyldimethyladamantane or a corresponding monool, can be fractionated from each other by vacuum distillation and used separately in preparing traction fluids.

Friction or traction drive systems for the transmission of power have been described in numerous prior art references. See, for example, the following:

1. Rounds, U.S. Pat. No. 3,394,603, dated July 30, 1968
2. Hamman et al., U.S. Pat. No. 3,411,369, dated Nov. 19, 1968
3. F. G. Rounds, J. OF CHEM. AND ENG. DATA, Vol. 5, No. 4, pps. 499-507 (October, 1960)
4. Hewko, Rounds and Scott, *Proceeding of the Symposium on Rolling Contact Phenomena*, pps. 157-185, Elsevier Publishing Co., Amsterdam (1962)

As can be seen from these references, special properties are required of the traction fluids used in friction drive systems. One desired property is a high coefficient of traction as measured, for example, by the test procedure described in reference (3) supra. As shown therein, most materials have traction coefficients (measured at a bearing speed of 600 ft./min.) less than 0.06, with the values for hydrocarbons usually falling in the range of 0.03-0.05. In comparison, bis-type products of the present invention, including the ethers as well as the hydrocarbon dimers, generally have traction coefficients measured in this manner in the neighborhood of 0.06 or higher. They are thus particularly valuable as additives for improving the traction coefficients of known types of traction fluid compositions. The liquid bis-type products of the invention are preferred for this purpose, but those which are normally solids also can be used to the extent that they are soluble in the base fluid at the temperatures at which it is required to operate in the friction drive system.

Such uses of bis-type hydrocarbon products of the present invention in traction fluid compositions are described and claimed in a copending application of I. N. Duling, D. S. Gates and R. E. Moore, Ser. No. 3,256, filed Aug. 19, 1969, now U.S. Pat. No. 3,648,531, issued Mar. 14, 1972, as a continuation-in-part of application Ser. No. 679,801, filed Nov. 1, 1967, now U.S. Pat. No. 3,597,356, issued Aug. 3, 1971, the latter being directed more generically to the use of adamantane compounds as components of traction fluids.

Such uses of the ether products are described and claimed in Ser. No. 232,510, filed Mar. 7, 1972, which is a continuation-in-part of said applications 3,256 and 679,801.

For the purpose of demonstrating specific embodiments of the invention, a series of runs was made in which various alkyladamantanes and/or alkyladamantanols were reacted in the presence of strong sulfuric acid but no other reactant. Each of these runs was carried out in the following manner:

One gram of the reactant compound was added to a flask containing 10 ml. of sulfuric acid of the selected strength and the mixture was agitated by means of a magnetic stirrer while the temperature was maintained at a selected level. At selected reaction times a 1 ml. sample of the reaction mixture was taken and quenched with 5-10 g. of ice. The resulting aqueous mixture was extracted with ethyl ether to remove all reaction products and the ether extract was then analyzed by GLC.

Twenty-four runs were made using reactants as tabulated below, and the data therefor are given in the accompanying Tables I-III.

| Run Nos. | Reactant (Designation) | Table |
|---|---|---|
| 1-4 | 1,3-dimethyladamantane (DMA) | I |
| 5-10 | 5,7-dimethyladamantanol-1 (DMA-ol) | I |
| 11-12 | 1:1 molar ratio of DMA and DMA-ol | I |
| 13-14 | 1-ethyl-3,5-dimethyladamantane (EDMA) | II |
| 15-16 | 3-ethyl-5,7-dimethyladamantanol-1 (EDMA-ol) | II |
| 17-18 | 1:1 molar ratio of EDMA and EDMA-ol | II |
| 19-20 | 1-ethyladamantane (EA) | III |
| 21-22 | 1-ethyl-3-methyladamantane (EMA) | III |

-continued

| Run Nos. | Reactant (Designation) | Table |
|---|---|---|
| 23 | (40:60 molar ratio of EMA and 1,3,5-trimethyladamantane (TMA)) | III |
| 24 | 1-n-propyl-3,5-dimethyladamantane (PDMA) | III |

In conjunction with these runs, preparative runs were also made in which individual reaction products were isolated by GLC and then tested for identification by IR, NMR and mass spectra.

In Tables I-III reactants are designated as indicated parenthetically in the foregoing list and, in addition, the following designations are used for various products obtained:

| adamantane | A |
|---|---|
| methyladamantane | MA |
| diethyladamantane | DEA |
| diethylmethyladamantane | DEMA |
| diethyldimethyladamantane | DEDMA |
| tetramethyladamantane | TTMA |
| di-n-propyldimethyladamantane | DPDMA |

For the hydrocarbon dimers, the ethers and the ketones produced in each run Tables I-III give the totals of each type of product. As previously stated, bis-type ether products are obtainable only for the reactant materials of Tables I and II. Product compositions are in area percents, which approximate weight percents.

TABLE I

Reactions of DMA and/or DMA-ol

| Run No. | Reagent | % $H_2SO_4$ | Approx. Temp., °C. | Time, hrs. | Product Composition, % | | | | | |
|---|---|---|---|---|---|---|---|---|---|---|
| | | | | | 1,3-DMA | 1,4-DMA | DMA-ol | Ketones | Dimers | Ethers |
| 1 | DMA | 96 | 25 | 3 | 99.5 | 0.5 | — | — | — | — |
| | | | | 4 | 98.6 | 1.4 | — | — | — | — |
| 2 | DMA | 96 | 65 | 12 | 51.2 | 0.8 | 3.6 | 2.1 | 42.3 | — |
| 3 | DMA | 97.5 | 65 | 12 | 50.0 | 0.9 | 1.9 | 2.6 | 44.6 | — |
| 4 | DMA | 100 | 25 | 0.25 | 32.6 | 0.2 | 44.3 | 2.2 | 5.9 | 0.6 |
| | | | | 0.5 | 23.5 | 0.2 | 44.7 | 2.5 | 10.7 | 3.5 |
| | | | | 1.0 | 16.0 | 0.2 | 36.0 | 2.3 | 21.2 | 13.2 |
| | | | | 4.0 | 10.2 | 0.2 | 16.7 | 2.3 | 32.5 | 34.3 |
| | | | | 6.0 | 9.6 | 0.2 | 16.2 | 2.2 | 20.2 | 46.5 |
| 5 | DMA-ol | 90 | 25 | 24 | 4.5 | — | 93.0 | 3.5 | — | — |
| 6 | DMA-ol | 96 | 5-10 | 6 | 1.0 | — | 98.0 | 1.0 | — | — |
| 7 | DMA-ol | 96 | 25 | 18 | 18.8 | 0.3 | 46.1 | 17.5 | 3.5 | 13.9 |
| | | | | 48 | 4.7 | 0.3 | 4.7 | 66.2 | 4.7 | 19.6 |
| 8 | DMA-ol | 96 | 50 | 3 | 25.6 | 0.3 | 29.1 | 15.0 | 9.3 | 20.9 |
| 9 | DMA-ol | 96 | 65 | 3 | 7.0 | 0.3 | 33.8 | 18.9 | 15.3 | 24.5 |
| | | | | 4 | 5.0 | 0.3 | 16.0 | 27.5 | 29.5 | 27.2 |
| 10 | DMA-ol | 100 | 25 | 0.50 | 3.0 | — | 72.7 | 2.3 | 0.8 (+11.7*) | 10.5 |
| | | | | 0.75 | 4.0 | — | 59.6 | 2.0 | 1.2 (+12.0*) | 22.8 |
| | | | | 1.67 | 5.0 | — | 23.0 | 3.0 | 4.2 (+3.5*) | 61.3 |
| | | | | 2.17 | 3.3 | — | 20.0 | 3.0 | 4.6 (+3.3*) | 65.4 |
| | | | | 2.67 | 2.9 | — | 13.0 | 2.0 | 5.3 (+2.0*) | 75.7 |
| 11 | DMA + DMA-ol (1:1) | 96 | 50 | 6 | 20.5 | 1.5 | 5.9 | 16.6 | 50.0 | 5.0 |
| 12 | " | 96 | 60 | 6 | 18.8 | 1.8 | 2.4 | 10.5 | 62.5 | 3.9 |

*Parenthetical values represent content of the olefinic dimer:4-(3,5-dimethyl-1-adamantyl)methylene-1-methyladamantane

TABLE II

Reactions of EDMA and/or EDMA-ol

| Run No. | Reagent | % $H_2SO_4$ | Approx. Temp., °C. | Time, hrs. | Product Composition, % | | | | | | | |
|---|---|---|---|---|---|---|---|---|---|---|---|---|
| | | | | | DMA | TTMA | EDMA | DEDMA | EDMA-ol | Ketones | Dimers | Ethers |
| 13 | EDMA | 97.5 | 10 | 0.2 | — | — | 53.8 | — | 44.4 | — | 1.8 | — |
| | | | | 0.5 | 2.5 | — | 21.0 | 1.0 | 3.5 | 2.0 | 70.0 | — |
| 14 | EDMA | 100 | 10 | 0.25 | 1.5 | 0.3 | 37.9 | 3.0 | 4.9 | 0.2 | 36.6 | 15.7 |
| | | | | 0.75 | 1.6 | 0.2 | 22.0 | 6.1 | 1.6 | 0.2 | 47.7 | 20.5 |
| | | | | 2.0 | 1.0 | 0.4 | 8.0 | 7.1 | 0.8 | 0.3 | 58.0 | 24.8 |
| 15 | EDMA-ol | 96 | 25 | 19 | 0.4 | — | 10.7 | 0.4 | 23.8 (+6.2*) | 2.2 | 38.3 | 18.0 |
| 16 | EDMA-ol | 96 | 65 | 3 | 1.0 | 0.2 | 7.8 | 9.0 | 1.6 | 1.0 | 73.2 | — |
| 17 | EDMA + EDMA-ol (1:1) | 96 | 25 | 18 | 2.9 | 1.0 | 33.9 | 6.7 | 4.3 | 2.4 | 29.2 | 15.8 |
| 18 | " | 100 | 25 | 2.0 | 2.6 | 0.9 | 17.9 | 7.0 | 0.2 | 0.7 | 47.1 | 23.5 |

*Parenthetical value represents DMA-ol content

TABLE III

Reaction of Other Alkyladamantanes

| Run No. | Reagent | % H₂SO₄ | Approx. Temp., °C | Time, hrs. | Product Composition, % | | | | | | | |
|---|---|---|---|---|---|---|---|---|---|---|---|---|
| | | | | | A | EA | DEA | Ketones | Dimers | | | |
| 19 | EA | 97.5 | 25 | 2 | 0.6 | 93.4 | 1.0 | — | 5.0 | | | |
| 20 | EA | 97.5 | 65 | 1 | 2.2 | 11.2 | 4.0 | 0.6 | 76.2 | | | |
| | | | | | MA | EMA | DEMA | EMA-ol | (unknown) | Dimers | | |
| 21 | EMA | 100 | 25 | 5 | 0.9 | 5.8 | 5.0 | 0.9 | 3.7* | 82.3 | | |
| 22 | EMA | 102 | 25 | 3 | 1.2 | 23.4 | 3.7 | 1.3 | — | 70.4 | | |
| | | | | | MA | TMA | EMA | TMA-ol | DEMA | EMA-ol | (unknown) | Dimers |
| 23 | TMA + EMA (40:60) | 100 | 25 | 3 | 1.1 | 34.8 | 8.3 | 2.0 | 1.3 | 0.5 | 3.2* | 47.6 |
| | | | | | DMA | PDMA | PDMA-ol | DPDMA | Dimers | | | |
| 24 | PDMA | 100 | 25 | 1 | 2.1 | 61.2 | 9.8 | 5.1 | 21.8 | | | |
| | | | | 3 | 0.9 | 4.7 | 0.5 | 7.8 | 86.1 | | | |

*Unknown products were neither ketones nor ethers.

Table I shows that bis-type products of either the dimer or ether type can be produced in good yields from 1,3-dimethyladamantane and/or its bridgehead monool by proper adjustment of reaction conditions. These products are linked in the manner shown in Equation 4 above. Runs 2 and 3 show that from the DMA hydrocarbon feed the hydrocarbon dimers can be made to preponderate in the reaction product, without any ether formation, by using an acid strength of about 96–98% $H_2SO_4$ and a moderately high temperature (65° C.). At room temperature and 96% acid strength (Run 1), reaction of the hydrocarbon feed is too slow to give an appreciable yield of products within a reasonable reaction time. However at 100% $H_2SO_4$ and room temperature, the hydrocarbon feed can yield substantial amounts of both dimers and ethers as shown by Run 4. Comparisons of Run 7 with Run 1 and of Run 10 with Run 4 indicate that the monool (DMA-ol) reacts more rapidly than its parent hydrocarbon (DMA) and is capable of giving large yields of the ethers at selected conditions. Run 7 also shows that a large amount of the ketones of DMA can be made from DMA-ol, if desired, by using an acid strength of about 96% at room temperature. A comparison of Run 12 with Run 2 shows that DMA can be made to react more rapidly by including DMA-ol along with it in the feed. Consequently it is advantageous when the fresh feed is DMA to recover DMA-ol from the reaction product and recycle it for further reaction. For example, the relatively large amount of DMA-ol formed in Run 7 can advantageously be recovered and recycled to expedite the reaction of the DMA.

In Run 10 an appreciable amount of the olefinic dimer previously described herein was formed, as shown by the parenthetically included data for this run.

The substitution of dimethyladamantanes and dimethyladamantanols in which one or more of the methyl and hydroxy substituents are located at nonbridgehead positions on the nucleus for the feed materials of Table I gives substantially equivalent results.

The results in Table II (Runs 13–18) show that ethyldimethyladamantane (EDMA) and/or its monool (EDMA-ol) react in a manner somewhat analogous to the dimethyladamantane reactants of Table I, likewise being capable of yielding ethers as well as dimers among the bis-type products. However, with these reactants the linkage moiety is an ethylene radical attached only to bridgehead carbon atoms of the respective adamantane nuclei. Furthermore, as previously explained, transalkylation of ethyl substituents between nuclei occurs to some extent and an appreciable amount of diethyldimethyladamantane (DEDMA) can appear among the products. Again, starting with nonbridgehead substituents in the EDMA or its monool does not greatly alter the results.

Table III shows results obtained with alkyladamantane reactants other than the dimethyl-substituted or ethyldimethyl-substituted reactants of Tables I–II. These other reactants readily yield hydrocarbon dimers but do not yield the ether products. Why ethers are obtained with the reactants of Tables I–II but not with alkyladamantanes of Table III is not understood at this time. Minor amounts of diethyl-substituted or dipropyl-substituted monomeric material resulting from transalkylation can be seen among the products of Runs 19–24. Runs 21 and 23 gave small amounts (3.7% and 3.2%) of product of unknown composition.

The saturated dimers and the ethers listed for Runs 2–12 had the structures shown in Equation 4 supra, each including the cis-type isomers and trans-type isomers in roughly equal proportions. Samples of these hydrocarbon dimer isomers and of the ether isomers collected from a preparative chromatographic column both were viscous colorless oils having the following properties:

| | Hydrocarbon Dimers (Formula I) | Ethers (Formula II) |
|---|---|---|
| Glass transition temperature, $T_g$ | −47° C. | — |
| KV at 100° F., cs | 2,777 | 10,591 |
| KV at 210° F., cs | 29.9 | 39.1 |
| Viscosity Index, ASTM | <0 | <0 |
| Viscosity Index, VTF* | −176 | −427 |

*Wright, ASTM Bulletin No. 215, pages 84–86, July, 1956

The higher viscosity for the ether isomers as compared to the hydrocarbon dimers is typical for the products obtained from EDMA as well as from DMA.

Traction coefficients for these dimer isomers and ether isomers obtained from DMA and/or DMA-ol were found to be extraordinarily high. For traction coefficients determined by the method described by Rounds, reference (3) supra, at a bearing speed of 600 ft./min., values as shown below are typical. For purpose of comparison, the traction coefficients determined in like manner for several other materials are also listed.

| | |
|---|---|
| dimer mixture from DMA | 0.063 |
| ether mixture from DMA | 0.059 |
| polypropylene | 0.046 |
| polybutene | 0.051 |
| naphthenic oil | 0.047 |
| diamyl naphthalene | 0.048 |
| di-2-ethylhexyl sebacate | 0.036 |
| ethyl ricinoleate | 0.030 |

These data illustrate the fact that both dimer and ether products provided by the present invention have remarkably high coefficients of traction and hence are particularly valuable as components of traction fluids. Any combination of the components of the dimer and ether fractions can advantageously be used as a traction fluid material.

The dimers and ethers obtainable from ethyldimethyladamantane and/or its monool for the runs shown in Table II are each a mixture of $C_{26}$, $C_{28}$ and $C_{30}$ compounds, the $C_{26}$ and $C_{30}$ compounds being the result of transalkylation of the ethyl substituent as previously described. The compositions of the dimer and ether fractions obtained from Run 18 were determined, with results as follows:

| | Dimer fraction | Ether fraction |
|---|---|---|
| $C_{26}$ | 16.1% (formula III) | 6.7% (formula VI) |
| $C_{28}$ | 57.2 (formula IV) | 85.7 (formula VII) |
| $C_{30}$ | 26.6 (formula V) | 7.6 (formula VIII) |

These data show that the $C_{26}$ and $C_{30}$ products are minor constituents of each fraction. Each of these fractions as well as any combination of at least two of the individual compounds are particularly useful as traction fluid material in view of the high coefficients of traction exhibited by the components.

Runs 21 and 22 of Table III represent conditions at which dimers can be made from ethylmethyladamantane in high yields. The dimer product is composed of a mixture of the $C_{24}$, $C_{26}$ and $C_{28}$ compounds shown in Equation 2 supra. Fractionation of the reaction products by GLC showed the following compositions for the dimer materials in these runs:

| | RUN 21 | RUN 22 |
|---|---|---|
| $C_{24}$ (formula XIII) | 13.9% | 11.3% |
| $C_{26}$ (formula IX) | 72.2 | 78.6 |
| $C_{28}$ (formula XIV) | 13.9 | 10.1 |

Although both the $C_{24}$ and $C_{28}$ compounds are normally solids when pure (MP of $C_{24}$ compound = 153° C.), the total mixture of these dimers is a viscous oil at room temperature having a high traction coefficient. Mixtures of the $C_{26}$ with either the $C_{24}$ or $C_{28}$ compound are also liquids useful as traction fluid material.

The total dimer product obtained from propyldimethyladamantane (PDMA) in Run 24 was fractionated by GLC and the fractions were analyzed. These proved to be the three dimer compounds shown in Equation 3. Melting points of the lowest and highest fractions, which were solids, were determined. Results were as follows:

| | % of Total Dimers | Melting Point, ° C. |
|---|---|---|
| $C_{27}$ (formula XI) | 17.5 | 70–74° |
| $C_{30}$ (formula X) | 62.1 | liquid at 20° C. |
| $C_{33}$ (formula XII) | 20.4 | 80–84° |

Again it can be seen that the products resulting from transalkylation were minor constituents of the total dimer product. While these two components when pure were solids, the mixture of compounds constituting the total dimers was a viscous oily liquid at room temperature. All of these compounds have high traction coefficients.

When other alkyladamantanes of the $C_{12}$–$C_{19}$ range and/or their monools as herein specified are substituted for the feed materials of the runs in Table III, substantially analogous results are obtained. However, such other reactants do not yield ethers like the reactants of Tables I and II.

For preparing a traction fluid material by the present process, it is advantageous to start with a mixture of alkyladamantanes of the $C_{12}$–$C_{14}$ range in which the alkyl groups are methyl and ethyl. Such feed mixture can be prepared from mixed tricyclic perhydroaromatics of the $C_{12}$–$C_{14}$ range by isomerization in accordance with procedures disclosed in either of the abovementioned U.S. Pat. Nos. 3,128,316 and 3,275,700. The mixture can then be treated with strong sulfuric acid in accordance with the invention to yield a multicomponent mixture of bis-type products of the $C_{22}$–$C_{30}$ range including dimer hydrocarbons and ethers. The entire multicomponent mixture can be recovered and used in traction fluid compositions. Alternatively, the mixed ethers can be recovered as a fraction separate from the mixed dimers, in view of the preferential solubility of the ethers in 98% $H_2SO_4$ as previously explained, and the two products can be used separately, if desired, as traction fluid components. A further alternative procedure involves separating the multicomponent mixture into cuts of varying molecular weights in accordance with boiling points, for example, by molecular distillation, and utilizing each cut separately as traction fluid material.

The symmetrical bis-type compounds which are normally solids that can be made by the present procedure have numerous other uses. They are useful, for example, as antiblocking agents in wax compositions for coating paper and as stiffening agents in candles. They also have utility as components of wax compositions useful for investment casting, in view of their stabilities, low melt viscosities and absence of any ash content after ignition. Individual bis-type compounds which are noncrystalline, or non-crystalline mixtures of the bis-type products, are useful as components of caulking compositions, potting compositions and adhesives.

In the following claims hydrogen atoms are omitted from the formulas shown. It is to be understood that any valences in the formulas which are unsatisfied are in fact satisfied by the appropriate number of hydrogen atoms.

The invention claimed is:

1. Method of reacting an alkyladamantane compound containing only methyl as the alkyl substituents to form a hydrocarbon dimer having two adamantane nuclei linked through a methylene radical which comprises:
   A. contacting a mixture consisting essentially of
      1. sulfuric acid having a strength of 94–102% $H_2SO_4$, and
      2. one or more compounds selected from the group consisting of methyl-substituted adamantanes and adamantanols having 2–3 methyl substituents, at a reaction temperature above the freezing point of said acid but below 100° C., the time of contacting and said acid strength being sufficient to result in substantial linkage to form hydrocarbon dimer in which the adamantane nuclei are inked through a methylene radical between bridgehead and nonbridgehead carbon atoms of the respective nuclei,
   B. and recovering said hydrocarbon dimer from the reaction mixture.

2. Method according to claim 1 wherein the acid concentration is in the range of about 96–100% $H_2SO_4$ and said temperature is in the range of 10°–75° C.

3. Method according to claim 2 wherein the methyl-substituted adamantane is dimethyladamantane.

4. Method according to claim 1 wherein the one or more compounds are selected from dimethyladamantane and dimethyladamantanol and said hydrocarbon dimer has a structure conforming to formula I.

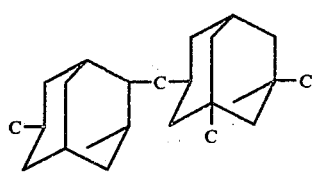

I

5. Method according to claim 4 wherein the strength of the sulfuric acid is at least 96% $H_2SO_4$ and sufficient to result in the formation also of an ether product having a structure conforming to formula II and said ether product also is recovered from the reaction mixture:

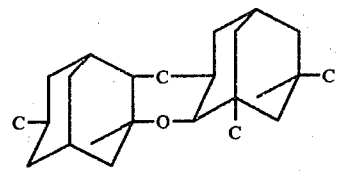

II

6. Method according to Claim 4 wherein the methyl substituted adamantanol is 3,5-dimethyladamantanol, the strength of the sulfuric acid is about 94–97% $H_2SO_4$, the reaction temperature is in the range of 20°–70° C., and from the reaction mixture a dimethyladamantanone product is also recovered.

7. As a composition of matter of bis-type adamantane product selected from the group consisting of (a) compounds having a structure conforming to formula I, (b) compounds having a structure conforming to formula II and (c) mixtures of compounds conforming both to formula I and formula II, wherein said formulas are:

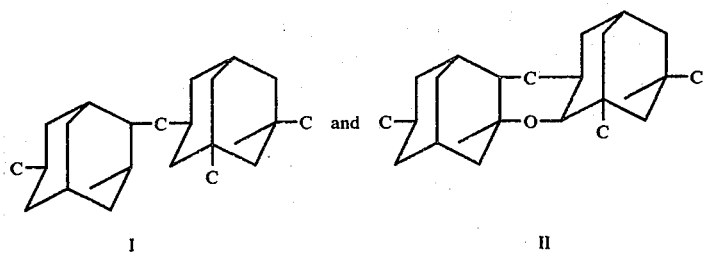

I and II

8. A compound according to claim 7 having a structure conforming to formula I.

9. A compound according to claim 7 having a structure conforming to formula II.

10. Method of reacting an alkyladamantane compound containing at least one alkyl substituent of the $C_2$–$C_3$ range to form a hydrocarbon dimer having two adamantane nuclei linked through an alkylene radical having 2–3 carbon atoms which comprises:
    A. contacting a mixture consisting essentially of
       1. sulfuric acid having a strength of 94–102% $H_2SO_4$, and
       2. one or more compounds selected from the group consisting of $C_{12}$–$C_{19}$ alkyladamantanes and alkyladamantanols having 1–3 alkyl substituents of the $C_1$–$C_3$ range with at least one of said substituents being of the $C_2$–$C_3$ range, at a reaction temperature above the freezing point of said acid but below 100° C., the time of contacting and said acid strength being sufficient to result in substantial linkage to form hydrocarbon dimer in which the adamantane nuclei are linked through an alkylene radical of the $C_2$-$C_3$ range,
    B. and recovering said hydrocarbon dimer from the reaction mixture.

11. Method according to Claim 10 wherein the one or more compounds contain an ethyl group and no higher alkyl substituent and said alkylene radical linking the nuclei is an ethylene radical.

12. Method according to Claim 45 wherein the acid concentration is in the range of about 96-100% $H_2SO_4$ and said temperature is in the range of 10-75° C.

13. Method according to Claim 12 wherein the alkyladamantane is ethyladamantane.

14. Method according to claim 12 wherein the alkyladamantane is ethylmethyladamantane.

15. Method according to claim 12 wherein the alkyladamantane is ethyldimethyladamantane.

16. Method according to claim 11 wherein the one or more compounds selected are from ethylmethyladamantane and ethylmethyladamantanol and hydrocarbon dimer recovered from the reaction mixture comprises a compound conforming to the following formula IX:

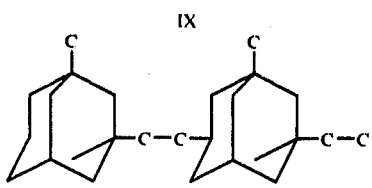

17. Method according to claim 11 wherein the one or more compounds are selected from ethyldimethyladamantane and ethyldimethyladamantanol, and hydrocarbon dimer recovered from the reaction mixture comprises compounds having structures conforming to the following formulas III, IV and V:

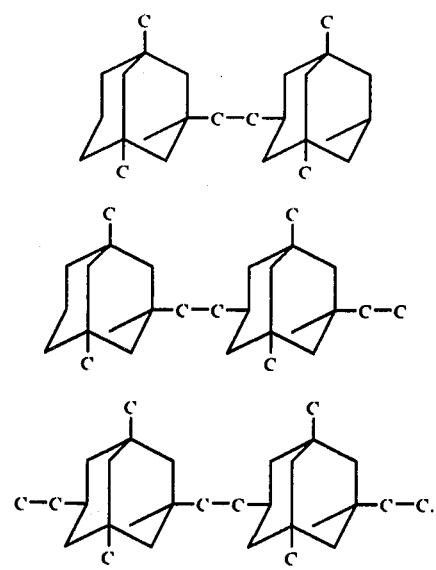

18. Method according to claim 17 wherein the strength of the sulfuric acid is at least 96% $H_2SO_4$ and sufficient to result in the formation of ether products conforming to formulas VI, VII and VIII and said ether products are also recovered from the reaction mixture:

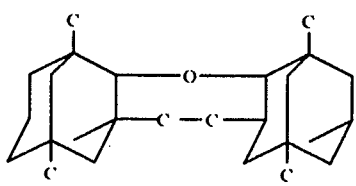

-continued

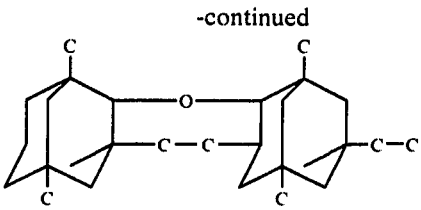

19. Method according to Claim 10 wherein the one or more compounds are selected from propyldimethyladamantane and propyldimethyladamantanol, and hydrocarbon dimer recovered from the reaction mixture comprises a compound conforming to the following formula X.

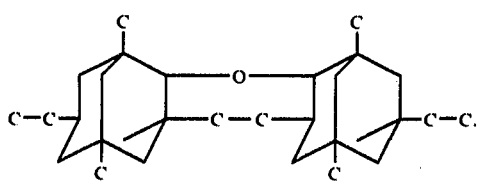

20. An adamantane hydrocarbon of structure conforming to any of the formulas IV, IX and X:

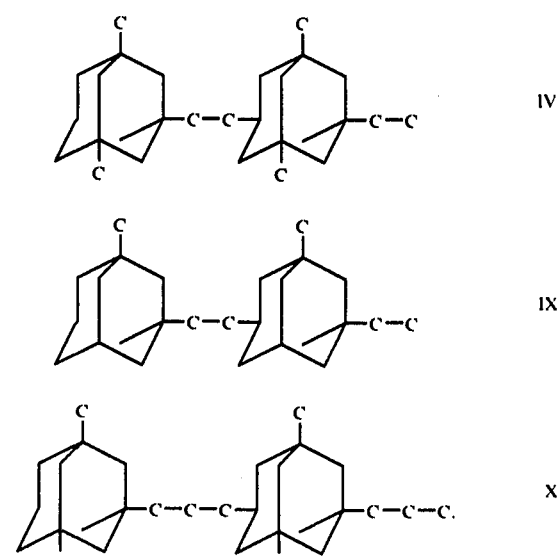

21. A liquid mixture of adamantane hydrocarbons comprising a compound having a structure conforming to formula IV with at least one other compound selected from those of structures conforming to formulas III and V:

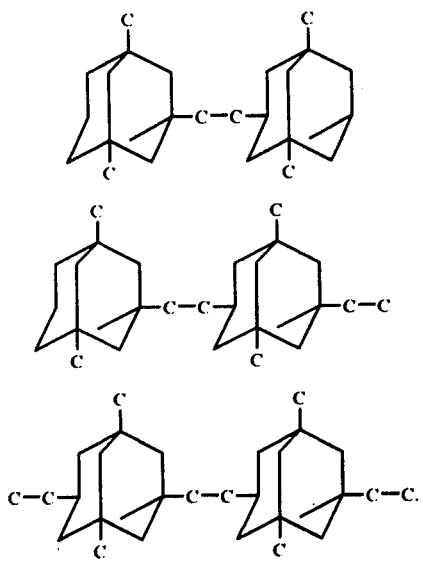

III

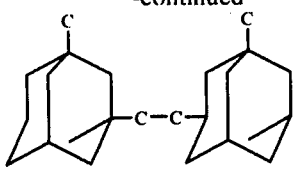

XIII

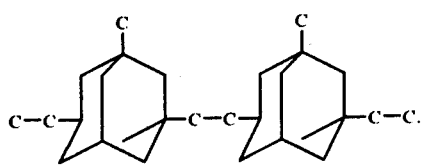

XIV

23. A liquid mixture of adamantane hydrocarbons comprising a compound having a structure conforming to formula X with at least one other compound selected from those of structures conforming to formulas XI and XII:

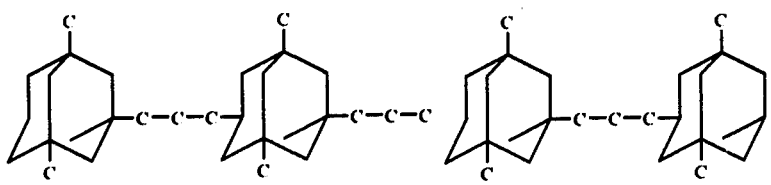

X          XI

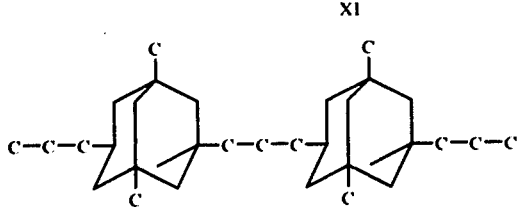

XII

24. An adamantane ether compound of structure conforming to any of the formulas VI, VII and VIII:

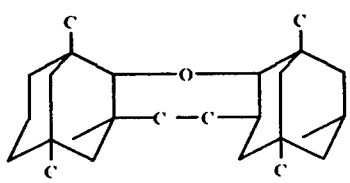

VI

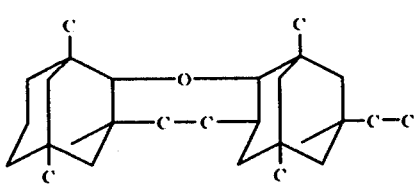

VII

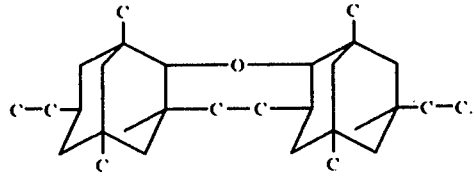

VIII

22. A liquid mixture of adamantane hydrocarbons comprising a compound having a structure conforming to formula IX with at least one other compound selected from those of structures conforming to formulas XIII and XIV:

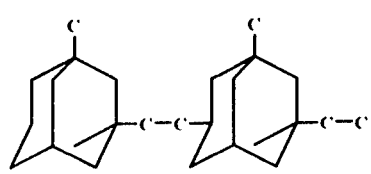

IX

* * * * *